United States Patent
Ranik et al.

(10) Patent No.: US 12,378,596 B2
(45) Date of Patent: Aug. 5, 2025

(54) WHOLE TRANSCRIPTOME ANALYSIS IN SINGLE CELLS

(71) Applicant: Roche Sequencing Solutions, Inc., Pleasanton, CA (US)

(72) Inventors: Martin Ranik, Santa Clara, CA (US); Florian Rubelt, Menlo Park, CA (US); Sedide Ozturk, Pleasanton, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 608 days.

(21) Appl. No.: 17/110,654

(22) Filed: Dec. 3, 2020

(65) Prior Publication Data

US 2022/0177950 A1 Jun. 9, 2022

(51) Int. Cl.
*C12Q 1/6809* (2018.01)
*C12Q 1/6853* (2018.01)
*C12Q 1/6869* (2018.01)
*C12Q 1/6876* (2018.01)

(52) U.S. Cl.
CPC ......... *C12Q 1/6809* (2013.01); *C12Q 1/6853* (2013.01); *C12Q 1/6869* (2013.01); *C12Q 1/6876* (2013.01); *C12Q 2521/101* (2013.01); *C12Q 2521/107* (2013.01); *C12Q 2521/327* (2013.01); *C12Q 2525/117* (2013.01); *C12Q 2525/155* (2013.01); *C12Q 2525/161* (2013.01); *C12Q 2525/173* (2013.01); *C12Q 2531/10* (2013.01); *C12Q 2537/149* (2013.01); *C12Q 2563/179* (2013.01); *C12Q 2563/185* (2013.01)

(58) Field of Classification Search
CPC ................ C12Q 1/6809; C12Q 1/6876; C12Q 2521/107; C12Q 2521/327; C12Q 2525/173
See application file for complete search history.

(56) References Cited

FOREIGN PATENT DOCUMENTS

| WO | WO-2014008447 A1 | * | 1/2014 | ......... C12N 15/1003 |
| WO | WO 2018/089550 A1 | * | 5/2018 | |
| WO | WO-2018201086 A1 | * | 11/2018 | ........... C12N 15/113 |
| WO | WO-2019126466 A1 | * | 6/2019 | ........... C12Q 1/6806 |

OTHER PUBLICATIONS

Kapteyn et al. "Incorporation of non-natural nucleotides into template-switching oligonucleotides reduces background and improves cDNA synthesis from very small RNA samples." BMC Genomics 11, 413 (2010). https://doi.org/10.1186/1471-2164-11-413 WO2018/089550A1, published May 17, 2018 (Year: 2018).*

Wang, Brian "Use of Template Switching Oligos (TS Oligos) for efficient cDNA library construction", Integrated DNA Technologies, published Mar. 8, 2017 (Year: 2018).*

* cited by examiner

*Primary Examiner* — Nancy J Leith
*Assistant Examiner* — Jessica D Parisi
(74) *Attorney, Agent, or Firm* — Charney IP Law LLC; Thomas M. Finetti

(57) ABSTRACT

The invention is a method of single cell transcriptome analysis. The method comprises detecting multiple transcripts in each individual cell of the plurality of cells by barcoding the transcripts with a cell-specific compound barcode formed using a DNA polymerase and a terminal transferase, optionally in a single enzyme such as a reverse transcriptase.

20 Claims, 3 Drawing Sheets

Specification includes a Sequence Listing.

BC = Barcode
TSO = Template Switch Oligo (barcode subunit)

WHOLE TRANSCRIPTOME ANALYSIS IN SINGLE CELLS

FIELD OF THE INVENTION

The invention relates generally to single cell analysis. More specifically, the invention relates to detecting multiple nucleic acid targets in individual cells without the need to isolate or segregate individual cells.

SEQUENCE LISTING

The contents of the electronic sequence listing (P35747-WO-1_ST25.txt; Size: 2,277 bytes; and Date of Creation: Apr. 27, 2023) is herein incorporated by reference in its entirety.

BACKGROUND OF THE INVENTION

Single cell analysis is starting to gain significance in understanding of biology and disease. Gene expression studies including whole transcriptome analysis reveal variation in gene expression between cells. Earlier methods required physical isolation of each cell under the microscope, see Tang et al. (2009) *mRNA-Seq, whole-transcriptome analysis of a single cell*, Nature Methods 6:377. U.S. Pat. No. 10,392,662 describes a technological solution that involves encapsulating individual cells in droplets and handling a water-oil emulsion so a plurality of individual reactions can occur at once. An alternative, more simple and elegant approach is described in U.S. Pat. No. 10,144,950. This novel approach termed "Quantum Barcoding" or "QBC" does not require separating individual cells in droplets or by any other means. Instead, QBC involves passing the entire plurality of cells through a series of split-pool rounds so a unique compound barcode could be assembled on each cell. In each round, a solution containing a plurality of cells is split into a number of reaction volumes, each containing a barcode sequence. After the barcode is attached to a target in each cell, the reaction volumes are pooled and split again so each cell receives the next-round barcode. Each cell follows a unique path through a series of barcode-containing wells and acquires a unique cell-associated compound barcode. The QBC method allows attaching these unique cell-associated compound barcodes to any target of interest in the cell: DNA, RNA, protein or other cellular target.

Assembly of compound barcodes on nucleic acids typically involves a ligation step, see Rosenberg, et al. (2018) *Single cell profiling of the developing mouse brain and spinal cord by split-pool barcoding*, Science, 360:176. Ligation requires additional reagents and reaction conditions and is less efficient than primer extension. Low efficiency is not acceptable for applications where nucleic acid targets are rare such as whole transcriptome analysis. There is an unmet need for a more robust method of barcoding and detecting nucleic acid targets in individual cells.

SUMMARY OF THE INVENTION

The invention comprises a method of assembling compound barcodes on nucleic acid targets in individual cells. Each of the multiple targets in an individual cell becomes labelled with the same cell-specific barcode. Barcodes are assembled from barcode subunits via a split-pool process. A unique property of the reverse transcriptase enzyme is employed to copy the barcode subunits and assemble a compound barcode.

In one embodiment, the invention is a method of detecting a plurality of target nucleic acids in a plurality of cells, the method comprising contacting the plurality of cells in a sample with an oligonucleotide primer for each target nucleic acid in the presence of a nucleic acid polymerase having a terminal transferase activity and extending the oligonucleotide primer to form a copy strand having one or more non-templated nucleotides at the 3'-end of the copy strand; for each target nucleic acid in each cell of the plurality of cells, forming a cell-characteristic compound barcode on the copy strand by sequentially attaching a series of barcode subunits to the 3'-end of the first copy strand by a split-pool process comprising one or more rounds of: distributing the sample into a first set of reaction volumes, each volume containing a first barcode subunit and a nucleic acid polymerase to extend the 3'-end of the copy strand to copy the first barcode subunit; combining the first set of reaction volumes into a pool; distributing the pool into a second set of reaction volumes, each volume containing a second barcode subunit and a nucleic acid polymerase to further extend the 3'-end of the copy strand to copy the second barcode subunit; determining the sequence of the extended copy strands including the cell-characteristic compound barcodes, thereby detecting the plurality of target nucleic acids in the plurality of cells. In some embodiments, the method further comprises a step of amplifying the extended copy strands including the cell-characteristic compound barcodes prior to sequencing.

In some embodiments, the oligonucleotide primer comprises a barcode and/or a universal amplification primer binding site. In some embodiments, barcode subunit to be copied comprises a universal amplification primer binding site.

In some embodiments, the target nucleic acid is DNA. In some embodiments, the target nucleic acid is RNA, e.g., messenger RNA and the oligonucleotide primer comprises a poly-dT sequence, or a target-specific sequence. In some embodiments, the oligonucleotide primer comprises a barcode.

In some embodiments, the nucleic acid polymerase is reverse transcriptase. The RT may have reduced RNaseH activity.

In some embodiments, the non-templated nucleotide is deoxycytosine.

In some embodiments, the barcode subunits comprise a portion complementary to the one or more non-templated nucleotides. In some embodiments, the barcode subunits comprise one or more modified nucleotides reducing the stability of subunit hybridization, such as iso-nucleotides located at the 5'-end of the barcode subunit.

In some embodiments, the invention is a kit for detecting a plurality of target nucleic acids in a plurality of cells, the kit comprising an oligonucleotide primer, a reverse transcriptase and a plurality of barcode subunits, wherein each barcode subunit comprises a poly-dG sequence. The barcode subunits may be present in a plurality of separate reaction volumes.

DETAILED DESCRIPTION OF THE INVENTION

Definitions

Figure 1:
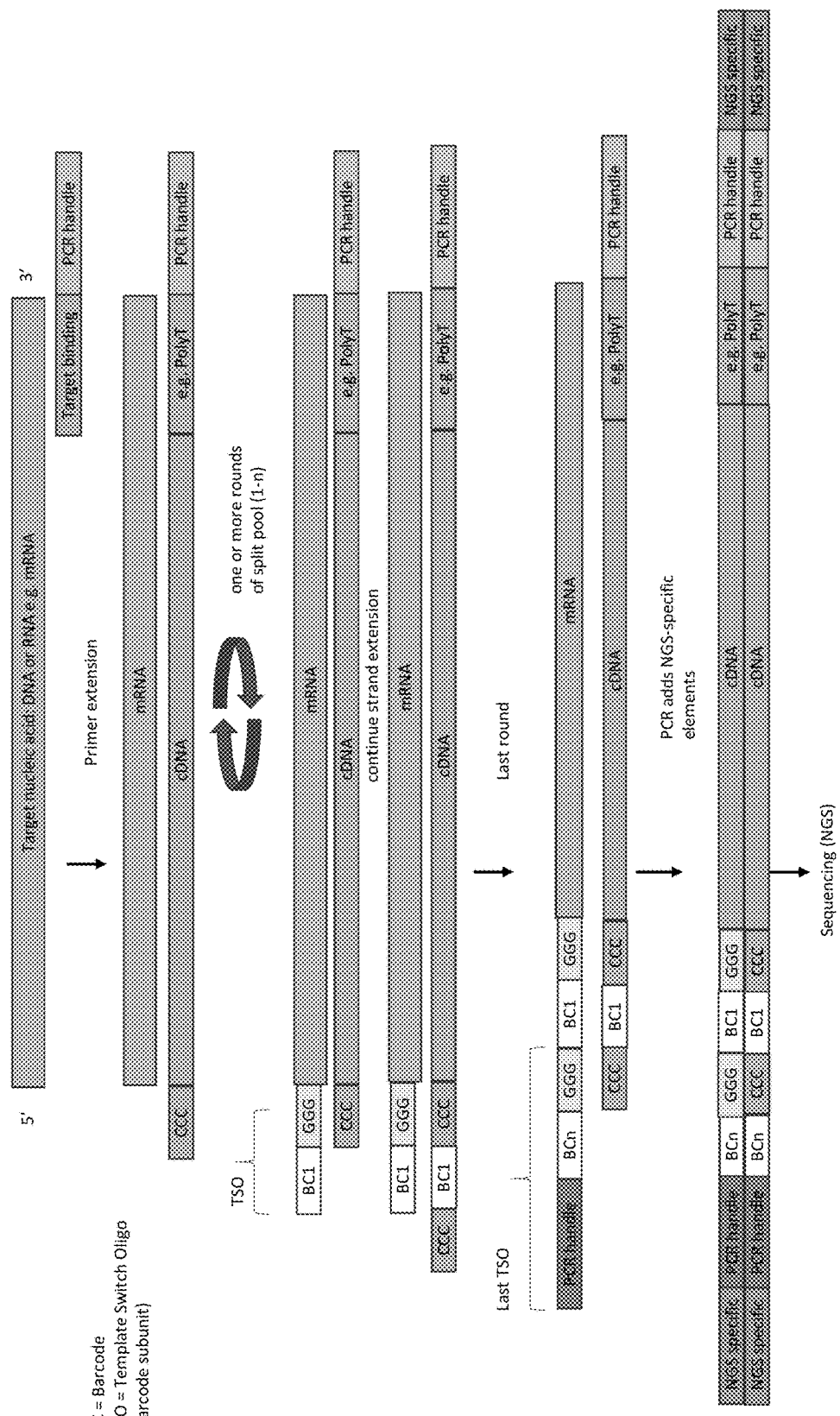
FIG. 1 is a schematic representation of the barcoding workflow.

The following definitions aid in understanding of this disclosure.

The term "adaptor" (or "adapter") refers to a nucleotide sequence that may be added to another sequence so as to import additional properties to that sequence. An adaptor can be single- or double-stranded, or may have both a single-stranded portion and a double-stranded portion.

The term "barcode" means a nucleotide sequence conferring identity to a molecule or a group of molecules sharing a common property or origin. A barcode may confer a unique identity to an individual molecule (and its copies). Such a barcode is a unique ID (UID) or unique molecular identifier (UMI). A barcode may confer an identity to an entire population of molecules (and their copies) coming from the same source (e.g., a sample). Such a barcode is a multiplex ID (MID) or sample ID (SID). To identify a nucleic acid molecule, a barcode need not be unique. Because a nucleic acid is also identified by its sequence, two nucleic acids having different sequences can share the same barcode and such barcode will act as a unique molecular barcode (UID or UMI).

The term "compound barcode" means a barcode assembled from barcode subunits. While each compound barcode is unique, two or more compound barcodes can share one or more barcode subunits among them.

The term "nucleic acid" refers to polymers of nucleotides (e.g., ribonucleotides and deoxyribonucleotides, both natural and non-natural) including DNA, RNA, and their subcategories, such as cDNA, mRNA, etc. A nucleic acid may be single-stranded or double-stranded and will generally contain 5'-3' phosphodiester bonds, although in some cases, nucleotide analogs may have other linkages as well as linkers, spacers and labels available in the art. Nucleic acids may include naturally occurring bases (adenosine, guanosine, cytosine, uracil and thymidine) as well as non-natural bases. Some examples of non-natural bases include those described in, e.g., Seela et al., (1999) *Helv. Chim. Acta* 82:1640. The non-natural bases may have a particular function, e.g., increasing the stability of the nucleic acid duplex, inhibiting nuclease digestion or blocking primer extension or strand polymerization.

The term "DNA polymerase" refers to an enzyme that performs template-directed synthesis of polynucleotides from deoxyribonucleotides. DNA polymerases include prokaryotic Pol I, Pol II, Pol III, Pol IV and Pol V, eukaryotic DNA polymerase, archaeal DNA polymerase, telomerase and reverse transcriptase. The term "thermostable polymerase," refers to an enzyme that is stable to heat, is heat resistant, and retains sufficient activity to effect subsequent polynucleotide extension reactions and does not become irreversibly denatured (inactivated) when subjected to the elevated temperatures for the time necessary to effect denaturation of double-stranded nucleic acids. In some embodiments, the following thermostable polymerases can be used: *Thermococcus litoralis* (Vent, GenBank: AAA72101), *Pyrococcus furiosus* (Pfu, GenBank: D12983, BAA02362), *Pyrococcus woesii, Pyrococcus* GB-D (Deep Vent, GenBank: AAA67131), *Thermococcus kodakaraensis* KODI (KOD, GenBank: BD175553, BAA06142; *Thermococcus* sp. strain KOD (Pfx, GenBank: AAE68738)), *Thermococcus gorgonarius* (Tgo, Pdb: 4699806), *Sulfolobus solataricus* (GenBank: NC002754, P26811), *Aeropyrum pernix* (GenBank: BAA81109), *Archaeglobus fulgidus* (GenBank: 029753), *Pyrobaculum aerophilum* (GenBank: AAL63952), *Pyrodictium occultum* (GenBank: BAA07579, BAA07580), *Thermococcus* 9 degree Nm (GenBank: AAA88769, Q56366), *Thermococcus fumicolans* (GenBank: CAA93738, P74918), *Thermococcus hydrothermalis* (GenBank: CAC18555), *Thermococcus* sp. GE8 (GenBank: CAC12850), *Thermococcus* sp. JDF-3 (GenBank: AX135456; WO0132887), *Thermococcus* sp. TY (GenBank: CAA73475), *Pyrococcus abyssi* (GenBank: P77916), *Pyrococcus glycovorans* (GenBank: CAC12849), *Pyrococcus horikoshii* (GenBank: NP 143776), *Pyrococcus* sp. GE23 (GenBank: CAA90887), *Pyrococcus* sp. ST700 (GenBank: CAC 12847), *Thermococcus pacificus* (GenBank: AX411312.1), *Thermococcus zilligii* (GenBank: DQ3366890), *Thermococcus aggregans, Thermococcus barossii, Thermococcus celer* (GenBank: DD259850.1), *Thermococcus profundus* (GenBank: E14137), *Thermococcus siculi* (GenBank: DD259857.1), *Thermococcus thioreducens, Thermococcus onnurineus* NA1, *Sulfolobus acidocaldarium, Sulfolobus tokodaii, Pyrobaculum calidifontis, Pyrobaculum islandicum* (GenBank: AAF27815), *Methanococcus jannaschii* (GenBank: Q58295), *Desulforococcus* species TOK, *Desulfurococcus, Pyrolobus, Pyrodictium, Staphylothermus, Vulcanisaetta, Methanococcus* (GenBank: P52025) and other archaeal B polymerases, such as GenBank AAC62712, P956901, BAAA07579)), thermophilic bacteria *Thermus* species (e.g., *flavus, ruber, thermophilus, lacteus, rubens, aquaticus*), *Bacillus stearothermophilus, Thermotoga maritima, Methanothermus fervidus,* KOD polymerase, TNA1 polymerase, *Thermococcus* sp. 9 degrees N-7, T4, T7, phi29, *Pyrococcus furiosus, P. abyssi, T. gorgonarius, T. litoralis, T. zilligii, T.* sp. GT, *P.* sp. GB-D, KOD, Pfu, *T. gorgonarius, T. zilligii, T. litoralis* and *Thermococcus* sp. 9N-7 polymerases. In some cases, the nucleic acid (e.g., DNA or RNA) polymerase may be a modified naturally occurring Type A polymerase. A further embodiment of the invention generally relates to a method wherein a modified Type A polymerase, e.g., in a primer extension, end-modification (e.g., terminal transferase, degradation, or polishing), or amplification reaction, may be selected from any species of the genus *Meiothermus, Thermotoga,* or *Thermomicrobium*. Another embodiment of the invention generally pertains to a method wherein the polymerase, e.g., in a primer extension, end-modification (e.g., terminal transferase, degradation or polishing), or amplification reaction, may be isolated from any of *Thermus aquaticus* (Taq), *Thermus thermophilus, Thermus caldophilus,* or *Thermus filiformis*. A further embodiment of the invention generally encompasses a method wherein the modified Type A polymerase, e.g., in a primer extension, end-modification (e.g., terminal transferase, degradation, or polishing), or amplification reaction, may be isolated from *Bacillus stearothermophilus, Sphaerobacter thermophilus, Dictoglomus thermophilum,* or *Escherichia coli*. In another embodiment, the invention generally relates to a method wherein the modified Type A polymerase, e.g., in a primer extension, end-modification (e.g., terminal transferase, degradation, or polishing), or amplification reaction, may be a mutant Taq-E507K polymerase. Another embodiment of the invention generally pertains to a method wherein a thermostable polymerase may be used to effect amplification of the target nucleic acid.

The term "reverse transcriptase" means and RNA-dependent DNA polymerase that synthesizes cDNA from an RNA template in the presence of a suitable primer. Wild-type reverse transcriptase possesses RNaseH activity that degrades RNA within the RNA-DNA hybrid. Some wild-type and engineered reverse transcriptases have reduced RNaseH activity. While a wild-type RNaseH+RT can be used, the enzymes with reduced RNaseH activity are especially suitable for the method of the instant invention. Reverse transcriptase also possesses a template switch activity requiring a template switch oligonucleotide (TSO) wherein upon reaching the end of the template, the reverse transcriptase switches from copying the template to copying the TSO.

The terms "polynucleotide" and "oligonucleotide" are used interchangeably. Polynucleotide is a single-stranded or a double-stranded nucleic acid. Oligonucleotide is a term sometimes used to describe a shorter polynucleotide. An oligonucleotide may be comprised of at least 6 nucleotides or about 15-30 nucleotides. Oligonucleotides are prepared by any suitable method known in the art, for example, by a method involving direct chemical synthesis as described in Narang et al. (1979) *Meth. Enzymol.* 68:90-99; Brown et al. (1979) *Meth. Enzymol.* 68:109-151; Beaucage et al. (1981) *Tetrahedron Lett.* 22:1859-1862; Matteucci et al. (1981) *J. Am. Chem. Soc.* 103:3185-3191.

The term "primer" refers to a single-stranded oligonucleotide which hybridizes with a sequence in the target nucleic acid and is capable of acting as a point of initiation of synthesis along a complementary strand of nucleic acid under conditions suitable for such synthesis. The primer may be partially or perfectly complementary to the target nucleic acid as long as it can form a stable hybrid with the target and be extended by a nucleic acid polymerase. The term "forward and reverse primers" refers to a pair of primers complementary and to opposite strands of the target nucleic acids at sites flanking the target sequence. Forward and reverse primers are capable of exponentially amplifying the target by polymerase chain reaction (PCR).

The term "sample" refers to any composition containing or presumed to contain target nucleic acid. This includes a sample of tissue or fluid isolated from an individual for example, skin, plasma, serum, spinal fluid, lymph fluid, synovial fluid, urine, tears, blood cells, organs and tumors, and also to samples of in vitro cultures established from cells taken from an individual, including the formalin-fixed paraffin embedded tissues (FFPET) and nucleic acids isolated therefrom. A sample may also include cell-free material, such as cell-free blood fraction that contains cell-free DNA (cfDNA) or circulating tumor DNA (ctDNA). In some embodiments, as will be clear to one skilled in the art from context, the term "sample" refers to a preparation that is obtained by processing (e.g., by removing or adding one or more components) a primary sample obtained from a patient. For example, such processing may include removing some tissue material (including blood components) from the sample and lysing any intact cells to release nucleic acids.

The term "sequencing" refers to any method of determining the sequence of nucleotides in the target nucleic acid.

The term "solid support" refers to any solid material capable of interacting with a capture moiety. A solid support can be a solution-phase support capable of suspension in a solution (e. g., a glass bead, a magnetic bead, or another like particle), or a solid-phase support (e.g., a silicon wafer, a glass slide, or the like). Examples of solution-phase supports include superparamagnetic spherical polymer particles such as DYNABEADS magnetic beads or Beckman Coulter AMPure solid phase reversible immobilization (SPRI) paramagnetic beads (ThermoFisher Scientific, Waltham, Mass.) or magnetic glass particles such as described in U.S. Pat. Nos. 6,274,386, 7,371,830, 6,870,047, 6,255,477, 6,746,874 and 6,258,531.

The terms "target sequence", "target nucleic acid" or "target" refer to a portion of the nucleic acid sequence in the sample which is to be detected or analyzed. The term target includes all variants of the target sequence, e.g., one or more mutant variants and the wild type variant.

The term "universal primer" and "universal priming site" refer to a primer and priming site not naturally present in the target sequence. Typically, the universal priming site is present in adapters or tail ends of target-specific primers. The universal primer can bind to and direct primer extension from the universal priming site.

Whole-transcriptome analysis of single cells is a useful new tool in the study of developmental biology and disease. U.S. Pat. No. 10,144,950 describes a method (termed "Quantum Barcoding" or "QBC") of labelling multiple targets, including multiple nucleic acid targets (DNA and RNA) in an individual cell with a unique-cell associated compound barcode. The compound barcode may be formed from nucleic acid subunits such as oligonucleotides comprising or consisting of a nucleic acid barcode. These barcode subunits are connected together for reading, e.g., by sequencing. One embodiment of QBC (U.S. Pat. No. 10,144,950) includes assembling compound barcodes from oligonucleotide subunits on nucleic acid targets. One of the ways to connect oligonucleotides is by ligation. Alternatively, a polymerase can copy a barcode subunit annealed to a template attached to an antibody as described in a U.S. application Ser. No. 16/250,974 "Identifying Multiple Epitopes in Cells" filed on Jan. 17, 2019. The instant invention is an improved method of nucleic acid barcoding by QBC. Specifically, the instant method improves on the existing QBC technology by utilizing the same polymerase enzyme for target enrichment and target barcoding when analyzing multiple nucleic acid targets in individual cells.

The instant invention is a novel method of analyzing gene expression (including whole transcriptome) in individual cells without the need to separate or encapsulate individual cells. The instant invention is a simplification and improvement of existing methods of single-cell whole transcriptome analysis.

A sample used in the method of the invention comprises any individual (e.g., non-human mammal, human subject or patient). The sample can also be an environmental or a plant sample containing cells. The sample can constitute any tissue or cell-containing fluid including cell culture. For example, the sample may be an organ (e.g., lymph node) or tumor biopsy or a blood or plasma sample. Sample can also consist of a subset of cells from a tissue, e.g., immune cells isolated from a tumor, tumor infiltrating lymphocytes (TILs). In some embodiments, the sample is a formalin-fixed, paraffin-embedded (FFPE) sample.

In some embodiments, the sample includes cell or subcellular compartments enclosing the target nucleic acids. In such embodiments, the method may include a step of permeabilizing the cells or subcellular compartments to allow access to target nucleic acids. Cells may be fixed in a methanol-buffer solution and resuspended in a suitable buffer with nuclease inhibitors (e.g., RNase inhibitors). See Chen et al., (2018) *PBMC Fixation and Processing for Chromium Single-Cell RNA Sequencing*, J. Transl Med. 16:198.

Primers used in the instant method may comprise a target specific sequence. The target specific sequence may be a gene-specific sequence, a motif-specific sequence (e.g., kinase domain specific sequence, RAS family-specific sequence, tri-nucleotide repeat sequence, etc.), or a random sequence (e.g., random hexamer sequence). The target specific sequence may also be a poly-dT sequence (e.g., dT$_{12-18}$). In some embodiments, the primer is a mixture of random primers and poly-dT primers.

Preferably, the target specific sequence is located in the 3'-portion of the primer. In addition to the target-specific region, the primer may comprise additional sequences. Preferably, these additional sequences are located to the 5'-end of the target-specific region. In other embodiments, it may be possible to include the additional sequences elsewhere within the primer as long as the target-specific region is capable of hybridizing to the target and driving the primer extension reaction as described below. The additional sequences within the primer may include one or more barcode sequences, such as a unique molecular identification sequence (UID) or a multiplex sample identification sequence (MID). The barcode sequences may be present as a single sequence or as two or more sequences.

In some embodiments, the additional sequences include sequences that facilitate ligation to the 5'-end of the primer. The primer may contain a universal ligation sequence that enables ligation of an adapter.

In some embodiments, the additional sequences include one or more a binding sites for one or more universal amplification primers. In some embodiments, the primer comprises a universal capture sequence that enables capture of the primer and primer extension products via hybridization to a capture oligonucleotide.

The invention is a method of simultaneously assessing one or more target nucleic acid sequences in a plurality of cells. The target sequences may include biomarkers of clinical relevance. The invention includes a method of simultaneously assessing one or more mRNA transcripts in a plurality of cells. In this embodiment, the targets include genes (or fragments of genes) whose level of expression is a biomarker of a disease or condition.

In some embodiments, the targets correspond to the type of cells used in the method. For example, if the method is applied to a plurality of immune cells, the genes characteristic of different types of cells and different conditions of the cell are used. In this embodiment, the targets include RNA transcripts of one or more of CD45, CD3, CD8, CD39, CD25, IL-7R, CD4, CXCR3, CCR6, CD3G, CD3D, CD3E, CD2, CD8A, GZMA FOXP3, CD19, CD79A, PDCD1, HAVCR2, IFNG, TNF, ITGAE, CXCR6.

In some embodiments, the method is applied to a plurality of tumor cells. In in this embodiment, the targets include RNA transcripts of one or more fusion genes common in cancer, e.g., one or more of ALK, NTRK1, FGFR2, FGFR3, RET, ROS1 and FIP1L1-PDGFRA. The targets may also include RNA transcripts of genes commonly mutated in cancer. The targets may include one or more genes listed in Table 3 (a)-(c) below.

TABLE 3 (a)

Additional genes detected by the method of the invention

| | | | |
|---|---|---|---|
| APC | ALK* | ERBB2 | NRAS |
| BRCA1 | BRAF | KRAS | PDGFRA |
| BRCA2 | DPYD | MET | ROS1* |
| EGFR | KIT | TR53 | UGT1A1 |
| RET | | | |

TABLE 3 (b)

Additional genes detected by the method of the invention

| | | | | | |
|---|---|---|---|---|---|
| APC | KRAS | ABL1 | FGFR3 | JAK3 | RAF1 |
| BRCA1 | MET | AKT1 | FLT1 | KDR | RNF43 |
| BRCA2 | TP53 | AKT2 | FLT3 | MAP2K1 | TERTpromoter |
| EGFR | KIT | ARAF | FLT4 | MAP2K2 | TSC1 |
| ERBB2 | NRAS | CDK6 | GATA3 | MTOR | TSC2 |
| ALK | PDGFRA | CSF1R | GNA11 | NFE2L2 | PTEN |
| BRAF | RET | CTNNB1 | GNAQ | NTRK1 | RB1 |
| DPYD | ROS1 | DDR2 | GNAS | PDGFRB | SMAD4 |
| AR | MSH2 | EZH2 | IDH1 | PIK3CA | SMO |
| CCND1 | MSH6 | FGFR1 | IDH2 | PIK3R1 | STK11 |
| CCND2 | NF2 | FGFR2 | JAK2 | PTCH1 | VHL |
| CCND3 | PDCD1LG2 | CDK4 | ESR1 | KEAP1 | UGT1A1 |
| CD274 | PMS2 | CDKN2A | FBXW7 | MLH1 | |

TABLE 3 (c)

Additional genes detected by the method of the invention

| | | | | | | |
|---|---|---|---|---|---|---|
| ABCC5 | CSMD1 | FAT1 | HTR1E | MAP7D3 | PIK3CA | SV2A |
| ABCG2 | CSMD3 | FBN2 | HTR2C | MKRN3 | PIK3CG | T |
| ACTN2 | CTNNB1 | FBXL7 | IFI16 | MMP16 | PKHD1L1 | THSD7A |
| ADAMTS12 | CTNND2 | FBXW7 | IL7R | MTX1 | POLE | TIAM1 |
| ADAMTS16 | CYBB | FCRL5 | INSL3 | MYH7 | POM121L12 | TMEM200A |
| ARFGEF1 | DCAF12L1 | FOXG1 | ITGA10 | MYT1L | PREX1 | TNFRSF21 |
| ASTN1 | DCAF12L2 | FRYL | ITSN1 | NAV3 | PTPLA | TNN |
| ASTN2 | DCAF4L2 | GBA3 | KCNA5 | NEUROD4 | RALYL | TNR |
| AVPR1A | DCLK1 | GBP7 | KCNB2 | NFE2L2 | RFX5 | TRHDE |
| BCHE | DCSTAMP | GJA8 | KCNC2 | NLGN4X | RIN3 | TRIM58 |
| BPIFB4 | DDI1 | GPR139 | KCNJ3 | NLRP3 | RNASE3 | TRPS1 |
| C6 | DLGAP2 | GRIA2 | KCTD8 | NMUR1 | ROBO2 | UGT3A2 |
| C6orf118 | DMD | GRIK3 | KEAP1 | NOL4 | SEMA5B | USH2A |
| CA10 | DNTTIP1 | GRIN2B | KIAA1211 | NPAP1 | SLC18A3 | USP29 |
| CACNA1E | DOCK3 | GRIN3B | KIF17 | NR0B1 | SLC39A12 | VPS13B |
| CDH12 | DSC3 | GRM1 | KIF19 | NRXN1 | SLC6A5 | WBSCR17 |
| CDH18 | DSCAM | GRM5 | KLHL31 | NXPH4 | SLC8A1 | WIPF1 |
| CDH8 | EGFLAM | GRM8 | KPRP | NYAP2 | SLFTRK1 | WSCD2 |
| CDH9 | EPHA5 | GSX1 | LPPR4 | OPRD1 | SLITRK4 | ZC3H12A |
| CDKN2A | EPHA6 | HCN1 | LRFN5 | P2RY10 | SLITRK5 | ZFPM2 |
| CHRM2 | EYS | HCRTR2 | LRP1B | PAX6 | SLPI | ZIC1 |
| CNTN5 | FAM135B | HEBP1 | LRRC7 | PCDH15 | SMAD4 | ZIC4 |
| CNTNAP2 | FAM151A | HECW1 | LRRTM1 | PDYN | SOX9 | ZNF521 |
| CPXCR1 | FAM5B | HS3ST4 | LRRTM4 | PDZRN3 | SPTA1 | ZSCAN1 |
| CPZ | FAM5C | HS3ST5 | LTBP4 | PGK2 | ST6GALNAC3 | KIT |

TABLE 3 (c)-continued

Additional genes detected by the method of the invention

| CRMP1 | FAM71B | HTR1A | MAP2 | PHACTR1 | STK11 | NRAS |
|-------|--------|-------|------|---------|-------|------|
| APC   | KRAS   | ALK   | PDGFRA | MET   | BRAF  | RET  |
| BRCA1 | BRCA2  | TP53  | DPYD | EGFR    | ERBB2 | UGT1A1 |

The primer extension step is performed by a nucleic acid polymerase. Depending on the type of nucleic acid being analysed, the polymerase may be a DNA-dependent DNA polymerase ("DNA polymerase") or an RNA-dependent DNA polymerase ("reverse transcriptase"). In some embodiments, a mixture of two or more polymerases is used to provide the combination of desired enzymatic activities.

In some embodiments, the polymerase is a reverse transcriptase (e.g., Moloney murine leukemia virus (MMLV) RT) that has reduced RNaseH activity. In some embodiments, the reverse transcriptase is active at elevated temperatures (up to 55° C.). In some embodiments, the polymerase possesses a terminal nucleotide transferase (terminal transferase) activity. Reverse transcriptase (e.g., MMLV RT) naturally possesses this activity. In some embodiments, in the presence of manganese (Mn) ions and dCTP, MMLV or MMLV-derived RT adds a stretch of dC nucleotides to the 3'-end of the copy strand. Under other conditions, MMLV or MMLV-derived RT adds a combination of dC and dA nucleotides.

In some embodiments, the polymerase possesses a terminal transferase activity and a template switch activity. For example, reverse transcriptase, e.g., MMLV or MMLV-derived RT during the first strand synthesis exhibits natural terminal transferase activity upon reaching the 5'-end of the copy strand. The stretch of added non-templated nucleotides functions as an anchoring site for a template switch oligo (TSO). Once TSO hybridizes to the stretch of non-templated nucleotides, the polymerase switches strands from copying the target (e.g., RNA) to copying the TSO.

In some embodiments, the DNA polymerase is a type A DNA polymerase (DNA-dependent DNA polymerase). Some DNA polymerases possess limited terminal transferase activity (Taq polymerase adding a single dA at the 3'-end of the copy strand). Other DNA polymerases do not possess detectable terminal transferase activity. In such embodiments, a separate terminal transferase enzyme is used to add non-templated nucleotides to the 3'-end of the copy strand.

In some embodiments, the DNA polymerase is a Hot Start polymerase or a similar conditionally activated polymerase. For the amplification step, a thermostable DNA polymerase is used, for example polymerase is a Taq or Taq-derived polymerase (e.g., KAPA 2G polymerase from KAPA Biosystems, Wilmington, Mass.).

The invention includes a method of assembling a compound barcode from barcode subunits. The barcode subunits are oligonucleotides comprising nucleic acid barcodes. Joined together, the barcode subunits form an ordered combination referred to as compound barcode. The compound barcode provides information necessary to identify the tagged entity, e.g., a cell in the plurality of cells. The barcode subunits may further comprise a nucleic acid sequence necessary to form a hybrid with the 3'-portion of the copy strand sufficient to enable copying of the barcode subunit by the nucleic acid polymerase. The barcode subunits may comprise a sequence complementary to the non-templated nucleotides at the 3'-end of the copy strand. In some embodiments, the barcode subunits comprise a poly dG sequence at the 3'-end.

Each barcode subunit can have from 2 nucleotides to 50 nucleotides. Each barcode subunit may comprise a pre-defined sequence, a random sequence and a combination thereof (see FIGS. 1, 2, 3). The use of a random-sequence barcode (UMI, FIGS. 1, 2, 3) can increase the diversity of barcodes being added. In case of a predefined sequence, a set of barcodes can be designed for an experiment.

In the workflow described below (FIGS. 1, 2, 3), two or more barcoded entities (e.g. cells) may share one or more barcode subunits in the same or different positions within the compound barcode. However, each barcoded entity has a unique ordered combination of barcoded subunits forming a unique compound barcode.

In some embodiments, to enhance stability of the hybrid formed between the copy strand and the barcode subunit, the subunit comprises modified nucleotides that increase stability of the hybrid as manifested by a higher melting temperature (Tm). The following bases may be used in place of traditional bases to increase Tm:

| Standard NTP | $T_m$-modified substitute base |
|---|---|
| ATP | 8-aza-7-Br-7-deaza-2,6-diaminopurine |
| CTP | 5-propynyl-dC |
| GTP | 8-aza-7-Br-7-deaza-dG |
| TTP | 5-propynyl-dU |

In some embodiments, the barcode subunits comprise modified nucleotides that inhibit annealing of the second subunit in the single round of assembly. In some embodiments, the modified nucleotide is one or more 5'-nucleotide isomers (isodC or isodG).

The invention provides a method comprising a number of split-pool rounds sufficient to generate enough unique compound barcodes to label each cell in a plurality of cells with a unique barcode. An exemplary calculation provided in U.S. Ser. No. 10/144,950 can be summarized as follows. The number of unique compound barcodes (B) can be determined according to the formula:

$B = \ln(1-C)/\ln(1-1/N)$, where

B is the number of compound barcodes
C is certainty of over representation of barcodes over cells
N is number of cells.

For example, starting with $N=10^6$ cells (1 million) and a 1/10 chance that two cells have the same barcode, the certainty of overrepresentation C=0.9999999. The number of unique compound barcodes needed (BC) would be:

$B = \ln(0.0000001)/(1-10^{-6}) \approx 16 \times 10^6$

For 16 million tags ($16 \times 10^6$), the number of rounds of split pool synthesis (X) of barcodes (B) from subunits (S) is determined by formula:

$X = \ln(B)/\ln(S)$

X is the number of rounds of split-pool synthesis
B is the number of compound barcodes
S is the number of subunits available to synthesize compound barcodes For example, to get 16 million compound barcodes out of 20 subunits, $$X = \ln(16 \times 10^6)/\ln 20 \cong 6$$

In some embodiments, the invention utilizes and an adaptor added to one or both ends of the target nucleic acid or a copy strand. Adaptors of various shapes and functions are known in the art (see e.g., PCT/EP2019/05515 filed on Feb. 28, 2019, U.S. Pat. Nos. 8,822,150 and 8,455,193).

The adaptor may be double-stranded, partially single stranded or single stranded. In some embodiments, a Y-shaped, a hairpin adaptor or a stem-loop adaptor is used wherein the double-stranded portion of the adaptor is ligated to the double stranded nucleic acid formed as described herein.

In some embodiments, the adaptor molecules are in vitro synthesized artificial sequences. In other embodiments, the adaptor molecules are in vitro synthesized naturally-occurring sequences. In yet other embodiments, the adaptor molecules are isolated naturally occurring molecules or isolated non naturally-occurring molecules.

The adaptor further comprises a primer binding site for at least one universal primer.

The double-stranded or partially double-stranded adaptor oligonucleotide can have overhangs or blunt ends. In some embodiments, the double-stranded DNA formed by the method described herein comprises blunt ends to which a blunt-end ligation can be applied to ligate a blunt-ended adaptor. In other embodiments, the blunt ended DNA undergoes A-tailing where a single A nucleotide is added to the blunt ends to match an adaptor designed to have a single T nucleotide extending from the blunt end to facilitate ligation between the DNA and the adaptor. Commercially available kits for performing adaptor ligation include AVENIO ctDNA Library Prep Kit or KAPA HyperPrep and HyperPlus kits (Roche Sequencing Solutions, Pleasanton, CA). In some embodiments, the adaptor ligated (adapted) DNA may be separated from excess adaptors and unligated DNA.

In one aspect, a universal blocking oligonucleotide includes a nonspecific region flanked by first and second specific regions. The nonspecific region includes, for example, a run of inosines that align with the sample index sequence when the universal blocking oligonucleotide is hybridized to the target adapter sequence. The specific regions of the universal blocking oligonucleotide are complementary to the invariant portion of the adapter sequence and include one or more melting temperature ($T_m$) modified bases to increase the $T_m$ of the blocking oligonucleotide-adapter duplex. Examples of $T_m$-modified base substitutes are illustrated in Table 1.

TABLE 4

| Standard NTP | Tm-modified substitute base |
|---|---|
| ATP | 8-aza-7-Br-7-deaza-2,6-diaminopurine |
| CTP | 5-propynyl-dC |
| GTP | 8-aza-7-Br-7-deaza-dG |
| TTP | 5-propynyl-dU |

In another aspect, unamplified nucleic acid libraries prepared with two different adapter sequences could be processed without blocking oligonucleotides if the adapter ends do not hybridize to one another. Adapter types suitable for this approach include forked and Y-shaped adaptors.

Ligation of the adaptor may be by single-strand ligation or a double-strand ligation. For single-strand ligation, the RT primer may comprise a universal ligation site. In such embodiments, the adapter having a double-stranded region and a single stranded overhang complementary to the universal ligation site in the primer may be annealed and ligated. Annealing of the single stranded 3'-overhang of the adapter to the universal ligation site at the 5'-end of the primer creates a double stranded region with a nick in the strand containing the RT primer (the copy strand). The two strands can be ligated at the nick by a DNA ligase or another enzyme, or a non-enzymatic reagent that can catalyze a reaction between the 5'-phosphate of the primer extension product and the 3'-OH of the adaptor.

The single-strand ligation method can be used to add the universal priming site to the opposite end of the copy strand. In such embodiment, a sequence-independent single-strand ligation method is employed. An exemplary method is described in a U.S. Application Pub. No. 20140193860. Essentially, the method uses a population of adapters where the single-stranded 3'-end overhang instead of having a universal ligation site, has a random sequence, e.g., a random hexamer sequence. In some embodiments of that method, the adapter also has a hairpin structure. Another example is a method enabled by ACCEL-NGS 1S DNA Library Kit (Swift Biosciences, Ann Arbor, Mich.).

The ligation step of the method utilizes a ligase or another enzyme with a similar activity or a non-enzymatic reagent. The ligase can be a DNA or RNA ligase, e.g., of viral or bacterial origin such as T4 or *E. coli* ligase, or thermostable ligases Afu, Taq, Tfl or Tth. In some embodiments, an alternative enzyme, e.g., topoisomerase can be used. Further, a non-enzymatic reagent can be used to form the phosphor-diester bond between the 5'-phosphate of the primer extension product and the 3'-OH of the adapter as described and referenced in US20140193860.

The invention relates to assembling cell-specific barcodes on target sequences in individual cells. The resulting barcoded target nucleic acid is subjected to nucleic acid sequencing, preferably, massively parallel single molecule sequencing. Analysing individual molecules by massively parallel sequencing typically requires a separate level of barcoding for sample identification and error correction. The use of molecular barcodes such as described in U.S. Pat. Nos. 7,393,665, 8,168,385, 8,481,292, 8,685,678, and 8,722,368. A unique molecular barcode is added to each molecule to be sequenced to mark molecule and its progeny (e.g., the original molecule and its amplicons generated by PCR). The unique molecular barcode (UID) has multiple uses including counting the number of original target molecules in the sample and error correction (Newman, A., et al., (2014) An ultrasensitive method for quantitating circulating tumor DNA with broad patient coverage, Nature Medicine doi:10.1038/nm.3519).

In some embodiments, unique molecular barcodes (UIDs) are used for sequencing error correction. The entire progeny of a single target molecule is marked with the same barcode and forms a barcoded family. A variation in the sequence not shared by all members of the barcoded family is discarded as an artefact. Barcodes can also be used for positional deduplication and target quantification, as the entire family represents a single molecule in the original sample (Newman, A., et al., (2016) *Integrated digital error suppression for improved detection of circulating tumor DNA*, Nature Biotechnology 34:547).

In some embodiments of the invention, the adaptor ligated to one or both ends of the barcoded target nucleic acid comprises one or more barcodes used in sequencing. A barcode can be a UID or a multiplex sample ID (MID or SID) used to identify the source of the sample where samples are mixed (multiplexed). The barcode may also be a combination of a UID and an MID. In some embodiments, a single barcode is used as both UID and MID. In some embodiments, each barcode comprises a predefined sequence. In other embodiments, the barcode comprises a random sequence. In some embodiments of the invention, the barcodes are between about 4-20 bases long so that between 96 and 384 different adaptors, each with a different pair of identical barcodes are added to a human genomic sample. In some embodiments, the number of UIDs in the reaction can be in excess of the number of molecules to be labelled. A person of ordinary skill would recognize that the number of barcodes depends on the complexity of the sample (i.e., expected number of unique target molecules) and would be able to create a suitable number of barcodes for each experiment.

The invention is a method of detecting a plurality of target nucleic acids in a plurality of cells. In some embodiments, the method comprises a step of contacting the plurality of cells in a sample with an oligonucleotide primer for each target nucleic acid in the presence of a nucleic acid polymerase. The nucleic acid polymerase possesses terminal transferase activity and polymerase activity. The polymerase extends the primer to form a copy strand and adds one or more non-templated nucleotides at the 3'-end of the copy strand. The method further comprises forming a cell-characteristic compound barcode on the copy strand (for each target nucleic acid in each cell of the plurality of cells) by sequentially attaching a series of barcode subunits to the 3'-end of the copy strand. The barcodes are added by a split-pool process. In some embodiments, the sample is distributed into a first set of reaction volumes (e.g., tubes or wells in a microwell plate) each volume containing a first barcode subunit so that the nucleic acid polymerase can extend the 3'-end of the copy strand to copy the first barcode subunit. The first set of reaction volumes is then pooled and distributed again into a second set of reaction volumes, each volume containing a second barcode subunit so that the nucleic acid polymerase can further extend the 3'-end of the copy strand to copy the second barcode subunit. These split-pool steps are repeated until the desired number of barcode subunits is added to the copy strand for each of the target nucleic acids. The barcoded strands are then sequenced by any available method. Optionally, the barcoded strands are amplified prior to sequencing.

In another embodiment, the present disclosure provides for a kit for detecting a plurality of target nucleic acids in a plurality of cells. In some embodiments, the kit comprises an oligonucleotide primer, a reverse transcriptase and a plurality of barcode subunits, wherein each barcode subunit comprises a poly-dG sequence. The kit may optionally contain buffers containing Mn ions for the terminal transferase activity of the reverse transcriptase. The kit may also contain optional reagents for DNA capture and purification, e.g., for separating the copy strand or barcoded copy strand from excess primers or excess barcode subunits.

In some embodiments, the method involves forming an expression library from a plurality of cells. The library consists of a plurality of barcoded copy strands generated from polynucleotides present in the plurality of cells. A library can be stored and used multiple times for further processing such as amplification or sequencing of the nucleic acids in the library.

In some embodiments, the library is subjected to a target enrichment process to select a subset of target nucleic acids for further analysis. For example, in an embodiment where the oligonucleotide primer comprises a poly-dT sequence to capture multiple mRNA targets, a target enrichment step may be used to capture mRNA transcripts of one or more genes of interest.

In some embodiments, the method of the invention includes one or more intervening purification steps. In some embodiments, the purification steps remove unused primers or unused barcode subunits prior to the next step of the method. In some embodiments, the primers and barcode subunits are separated from the larger-size copy strands by a size-exclusion method, for example, gel electrophoresis, chromatography or isotachophoresis or epitachophoresis.

In some embodiments, purification is by affinity binding. In variations of this embodiment, the affinity is to the specific target sequence (sequence capture). In other embodiments, the primer comprises an affinity tag. Any affinity tag known in the art can be used, such as biotin or an antibody or an antigen for which a specific antibody exists. The affinity partner for the affinity tag may be present in solution, e.g., on a solution-phase solid support, such as suspended particles or beads, or bound to solid-phase support. In the course of affinity purification, unbound components of the reaction mixture are washed away. In some embodiments, additional steps are taken to remove unused primer. In some embodiments, the affinity capture alters the charge of the primer extension product. For example, the inclusion of one or more biotinylated nucleotides and binding or streptavidin thereto creates an altered charge on the nascent nucleic acid strand. The altered charge can be utilized for separation of the nascent strand (the primer extension product) by isotachophoresis or epitachophoresis.

In some embodiments, the invention includes a step of amplification prior to the sequencing step. The amplification utilizes an upstream primer and a downstream primer. In some embodiments, at least one primer is a target-specific primer, i.e., has a sequence complementary to the target sequence. In some embodiments, one or both primers are universal primers. A universal primer may be paired with another universal primer (of the same or different sequence). In other embodiments, the universal primer is paired with a target-specific primer.

A universal primer binding site may be appended to the target nucleic acid in various ways. In some embodiments, the universal primer binding site is present in the 5'-portion of the RT primer. Similarly, the universal primer binding site can be present in the 5'-end of the last barcode subunit to be added to the compound barcode. In other embodiments, the universal primer binding site is present in an adaptor and is added to one or both ends of the target nucleic acid by ligation.

In some embodiments, the barcoded copy strands or a library of barcoded copy strands from the plurality of cells are sequenced. Any of a number of sequencing technologies or sequencing assays can be utilized. The term "Next Generation Sequencing (NGS)" as used herein refers to sequencing methods that allow for massively parallel sequencing of clonally amplified molecules and of single nucleic acid molecules.

Non-limiting examples of sequence assays that are suitable for use with the methods disclosed herein include nanopore sequencing (US Pat. Publ. Nos. 2013/0244340, 2013/0264207, 2014/0134616, 2015/0119259 and 2015/0337366), Sanger sequencing, capillary array sequencing, thermal cycle sequencing (Sears et al., *Biotechniques*, 13:626-633 (1992)), solid-phase sequencing (Zimmerman et al., *Methods Mol. Cell Biol.*, 3:39-42 (1992)), sequencing with mass spectrometry such as matrix-assisted laser desorption/ionization time-of-flight mass spectrometry (MALDI-TOF/MS; Fu et al., *Nature Biotech.*, 16:381-384 (1998)), sequencing by hybridization (Drmanac et al., *Nature Biotech.*, 16:54-58 (1998), and NGS methods, including but not limited to sequencing by synthesis (e.g., HiSeq™, MiSeq™, or Genome Analyzer, each available from Illumina), sequencing by ligation (e.g., SOLiD™, Life Technologies), ion semiconductor sequencing (e.g., Ion Torrent-, Life Technologies), and SMRT® sequencing (e.g., Pacific Biosciences).

Commercially available sequencing technologies include: sequencing-by-hybridization platforms from Affymetrix Inc. (Sunnyvale, Calif.), sequencing-by-synthesis platforms from Illumina/Solexa (San Diego, Calif.) and Helicos Biosciences (Cambridge, Mass.), sequencing-by-ligation platform from Applied Biosystems (Foster City, Calif.). Other sequencing technologies include, but are not limited to, the Ion Torrent technology (ThermoFisher Scientific), and nanopore sequencing (Genia Technology from Roche Sequencing Solutions, Santa Clara, Cal.); and Oxford Nanopore Technologies (Oxford, UK).

In some embodiments, the sequencing step involves sequence aligning. In some embodiments, aligning is used to determine a consensus sequence from a plurality of sequences, e.g., a plurality having the same unique molecular ID (UID). The molecular ID is a barcode that can be added to each molecule prior to sequencing or if amplification step is included, prior to the amplification step. In some embodiments, a UID is present in the 5'-portion of the RT primer. Similarly, a UID can be present in the 5'-end of the last barcode subunit to be added to the compound barcode. In other embodiments, a UID is present in an adaptor and is added to one or both ends of the target nucleic acid by ligation.

In some embodiments, a consensus sequence is determined from a plurality of sequences all having an identical UID. The sequenced having an identical UID are presumed to derive from the same original molecule through amplification. In other embodiments, UID is used to eliminate artifacts, i.e., variations existing in the progeny of a single molecule (characterized by a particular UID). Such artifacts resulting from PCR errors or sequencing errors can be eliminated.

In some embodiments, the quantity of each sequence in the sample can be determined by quantifying relative numbers of sequences with each UID among the population having the same multiplex sample ID (MID). Each UID represents a single molecule in the original sample and counting different UIDs associated with each sequence variant can determine the fraction of each sequence variant in the original sample, where all molecules share the same MID. A person skilled in the art will be able to determine the number of sequence reads necessary to determine a consensus sequence. In some embodiments, the relevant number is reads per UID ("sequence depth") necessary for an accurate quantitative result. In some embodiments, the desired depth is 5-50 reads per UID.

Figure 2:
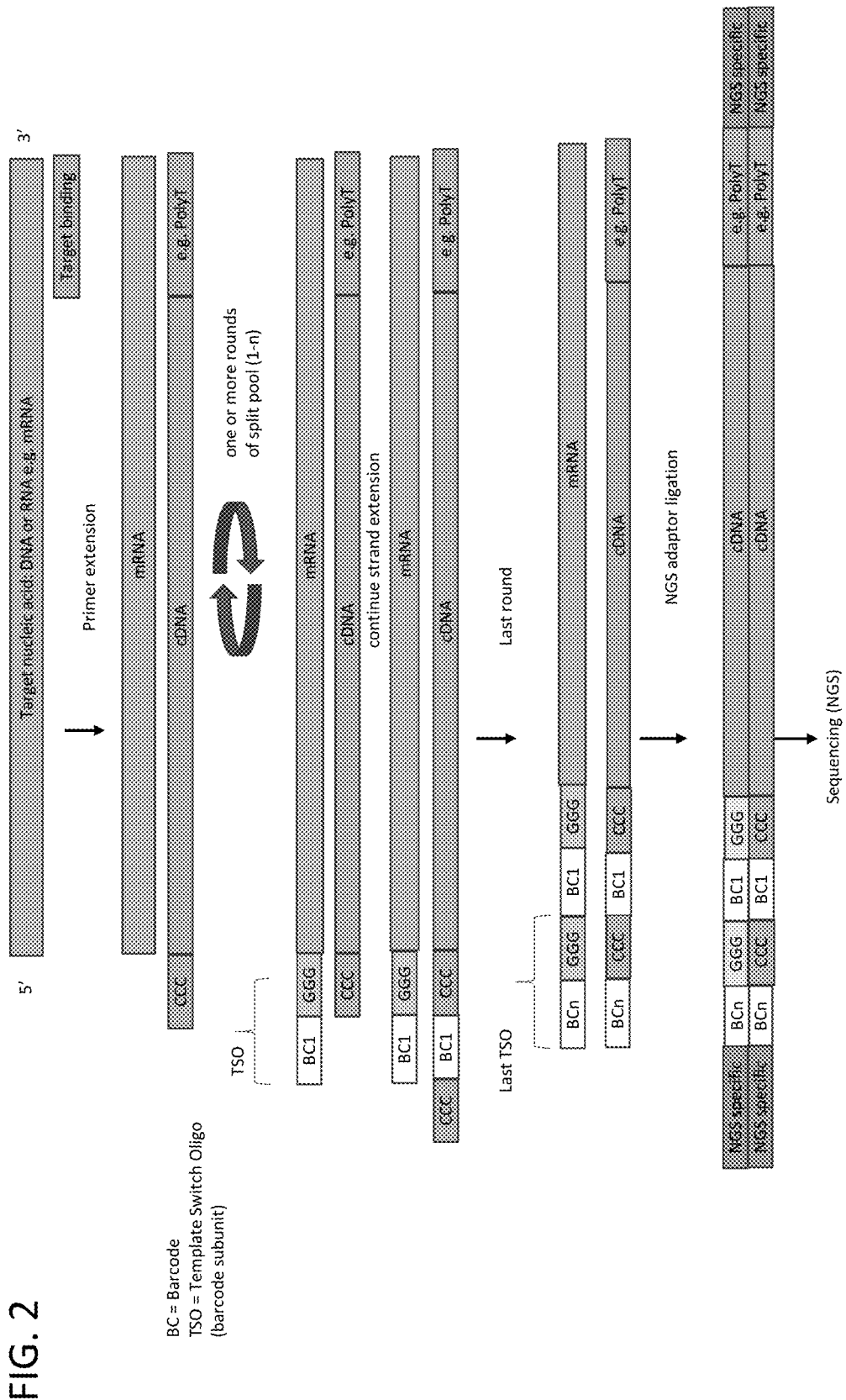
FIG. 2 is a schematic representation of another embodiment of the barcoding workflow.
Figure 3:
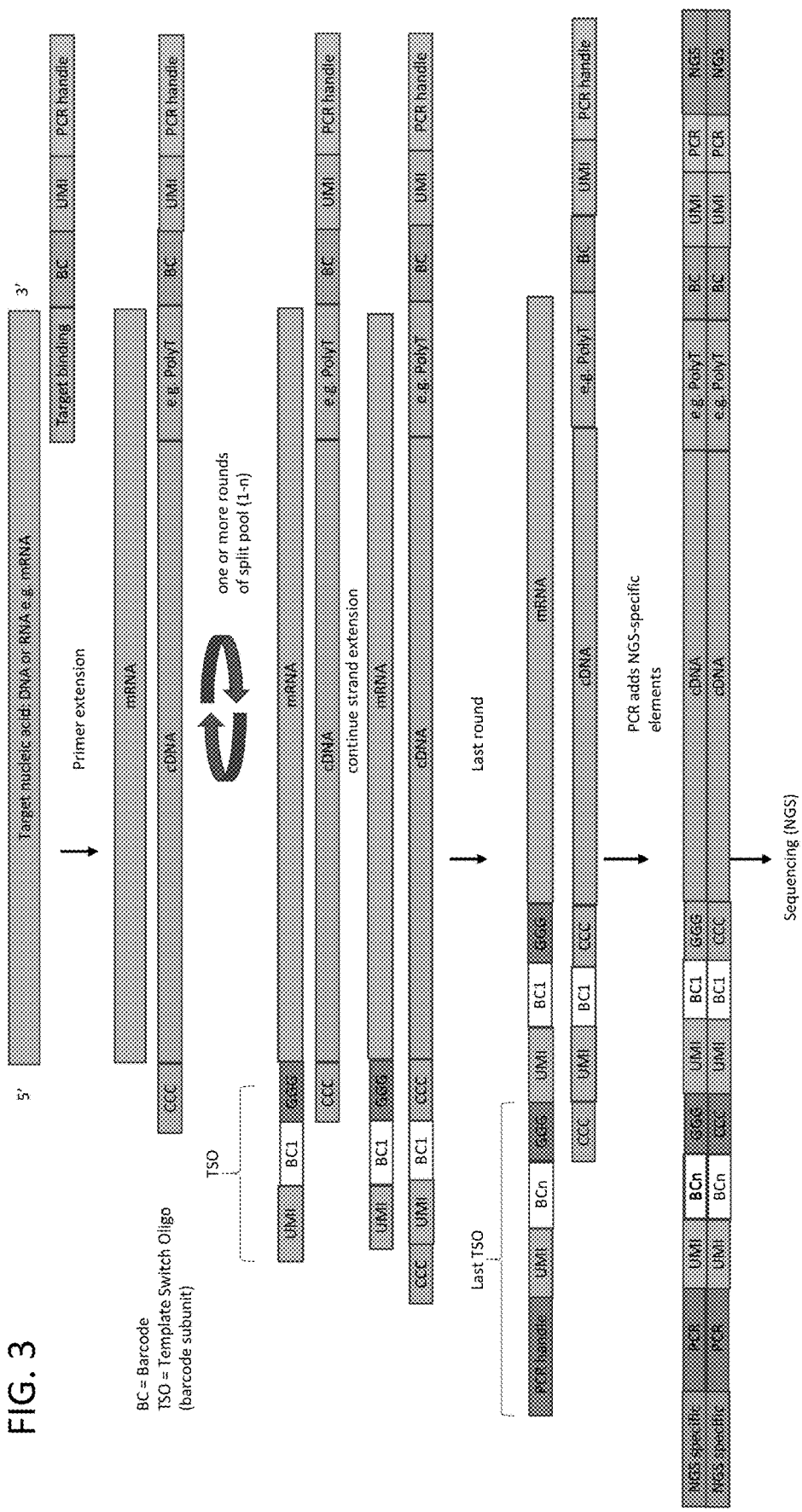
FIG. 3 is a schematic representation of yet another embodiment of the barcoding workflow.

The instant invention is described in more detail in reference to FIGS. 1, 2 and 3. The figures illustrate several embodiments of the invention and are not to be construed as limiting with respect to optional features as well as the order or number of steps in the claimed method. The embodiments shown in FIGS. 1, 2 and 3 have the same steps but differ in the number of optional features. The workflow is described in relation to FIG. 1 and where appropriate, FIGS. 2 and 3 are referenced to illustrate optional features.

Referring to FIG. 1, the first step is contacting a single-stranded target nucleic acid (DNA or RNA of any type) with a primer. The primer has a 3'-portion substantially complementary to the target nucleic acid to ensure hybridization and extension. In the example on FIG. 1, the complementary sequence is poly-dT to hybridize to poly-dA end of mRNA. Other examples of the complementary sequence include a gene-specific sequence, a motif-specific sequence (e.g., kinase domain specific sequence, RAS family-specific sequence, tri-nucleotide repeat sequence, etc.), or a random sequence (e.g., random hexamer sequence). In some embodiments, the primer sequence is a combination of random sequences and poly-dT sequences.

The primer may comprise a 5'-portion with an additional sequence. The primer in FIG. 1 is shown to have a primer binding site, e.g., an amplification primer binding site. The primer in FIG. 2 lacks any additional sequences while the primer in FIG. 3 has a primer binding site and a barcode. The barcode comprises a random unique molecular identifier barcode (UMI) (also known as UID) uniquely identifies the copy strand in a cell. The barcode also comprises a defined barcode (BC). Optionally, the sample can be distributed into a series of reaction volumes, each comprising the primer with a different barcode (BC). The diversity of barcodes (BC) in different reaction volumes adds to the diversity created by the compound barcode described below to create a unique identifier for an individual cell.

Referring further to FIG. 1, the next step is extension of the primer to copy the target nucleic acid with a nucleic acid polymerase. The polymerase is shown to form a copy strand and to add non-templated nucleotides to the 3'-end of the copy strand. FIG. 1 shows a non-templated addition of $dC_3$, which is characteristic of certain types of reverse transcriptases in the presence of manganese ions. Other nucleotide sequences are possible and the 3'-end of the copy strand. For example, reverse transcriptase can add other nucleotides (such as dA or dA/dC combination) under different buffer conditions. Taq polymerase adds a single dA to the 3'-end of the copy strand. It is further possible to separate the functions of the polymerase and terminal transferase so that the two functions are performed by separate enzymes.

Referring further to FIG. 1, the next step is a split-pool procedure where the reaction mixture is split into a number of reaction volumes (e.g., wells in a microwell plate, tube strips or other type of separate volumes) where each volume contains a unique barcode subunit oligonucleotide. As shown in FIG. 1, the barcode subunit has a complementary sequence that allows it to anneal to the stretch of non-templated nucleotides at the end of the copy strand. The annealing enables copying of the barcode subunit by the nucleic acid polymerase extending the copy strand. As shown in FIG. 1, in addition to the sequence complementary to the non-templated portion of the copy strand, the barcode subunit has the barcode sequence (BC1). The barcode can be a predefined sequence as shown in FIGS. 1 and 2. As shown in FIG. 3, the barcode is further enhanced with a random sequence (UMI).

Referring further to FIG. 1, the step of adding barcode subunits is repeated until the desired length compound barcode is assembled at the end of the copy strand. Each addition of the barcode subunit is performed by a split-pool process. After the barcode subunit has been copied by the polymerase, the reactions are pooled and split into the next round of reaction volumes, each volume comprising a unique barcode subunit oligonucleotide for the next round of barcode assembly. In each round, the polymerase adds a strand of non-templated nucleotides to the end of the extended copy strand to enable annealing of the next round of barcode subunit oligonucleotide.

In some embodiments, there is an optional purification step that removes unused oligonucleotides such as unused barcode subunits and primers. In some embodiments, the purification utilizes an exonuclease, e.g., Exonuclease I. Removing the unused oligonucleotides as well as optionally, the exonuclease may require a buffer exchange including by affinity binding as described in the preceding section.

In some embodiments, the use of additional barcodes (e.g., the 5'-barcode on the oligonucleotide primer) as well as UMIs minimizes the number of rounds of compound barcode assembly. With fewer rounds, especially a single round, the purification step can be avoided.

The steps of annealing to the copy strand and extension of the copy strand to copy the next barcode subunit may be repeated until the desired length of barcode is assembled. One of skill in the art is able to calculate the length of the barcode subunit and number of rounds of assembly needed to match the number of entities (e.g., cells) to be tagged with unique compound barcodes.

The template switch activity of RT is known and is in commercial use, see Zhu et al., (2001) *Reverse transcriptase template switching: a SMART approach for full-length cDNA library construction*, Biotechniques, 30:892 and U.S. Pat. Nos. 5,962,271 and 5,962,272. This property of RT is used to enrich for full-length cDNA (SMARTER PCR cDNA Synthesis kit (Clontech, Mountain View, Cal.)). More recently, this property of RT has found use in next-generation sequencing (NGS) where the template switch oligonucleotide (TSO) acts as a sequencing adaptor, i.e., comprises NGS-specific sequence elements, see Ohtsubo, et al., (2018) *Optimization of single strand DNA incorporation reaction by Moloney murine leukaemia virus reverse transcriptase*, DNA Research, 25:477, and SMARTer® smRNA Sequencing kit for Illumina (Takara Bio., Mountain View, Cal.)

The invention comprises a step of concatenating (adding multiple) TSOs to a single copy strand of the target nucleic acid. In the art, addition of multiple TSOs is considered an undesirable artefact to be minimized or avoided. For example, Kapteyn et al. ((2010) *Incorporation of non-natural nucleotides into template-switching oligonucleotides reduces background and improves cDNA synthesis from very small RNA samples*, BMC Genomics, 11:413) teach incorporating modified nucleotides at the 5'-end of TSO to prevent the second template switch from occurring. Ohtsubo et al. (supra) use a 5'-biotinylated oligonucleotide to prevent concatenation. The inventors devised a novel use of this enzymatic property. The instant invention includes the use of 5'-nucleotide isomers (isodC) in barcode subunits and shortened incubation time to minimize concatenation in the same round but enable the next round of adding barcode subunits. The instant method finds utility in the undesirable concatenation ability of the polymerase by harnessing it to assemble a compound barcode from multiple TSOs.

Referring further to FIG. 1, the barcode subunit oligonucleotide added in the last round of assembly may have additional sequences in the 5'-portion of the oligonucleotide. As shown in FIGS. 1 and 3, the last barcode subunit has an amplification primer binding site. The barcode subunit may also comprise a sequencing primer binding site, a unique molecular barcode and sample barcode. In FIGS. 1 and 3, the sequencing method-specific or instrument-specific elements are added during pre-sequencing amplification via 5'-portions of amplification primers. FIG. 2 shows adding sequencing instrument-specific elements by ligating adaptors to one or both ends of the nucleic acid to be sequenced.

Referring further to FIGS. 1 and 2, the workflow yields a double-stranded nucleic acid fragment comprising the copy strand of the target nucleic acid and a cell-specific compound barcode assembled at one end of the copy strand by extending the copy strand. In FIG. 3, the double-stranded nucleic acid fragment further comprises a barcode at the end opposite of the compound barcode.

In some embodiments, the method further comprises assessment of a status of a subject (e.g., a patient). In some embodiments, the method further comprises determining in the patient's sample, the sequence and optionally amount of RNA transcripts of multiple biomarkers of disease. In one example, the invention includes assessing the status of a patient by determining expression of immune cell biomarkers in individual immune cells from an immune cell population isolated from the patient. The immune cell biomarkers may be selected from markers of T-cell type, T-cell exhaustion, T-cell activation, markers of tissue-resident memory cell, markers and markers of tumor-reactive T-cells. These markers may include RNA transcripts of one or more of CD45, CD3, CD8, CD39, CD25, IL-7R, CD4, CXCR3, CCR6, CD3G, CD3D, CD3E, CD2, CD8A, GZMA FOXP3, CD19, CD79A, PDCD1, HAVCR2, IFNG, TNF, ITGAE, CXCR6, (see Yost et al. (2019) *Clonal replacement of tumor specific T-cells following PD-1 blockade*, Nature Medicine, doi.org/10.1038/s41591-019-0522-3. The method further comprises diagnosis of disease in the patient or selecting or changing a treatment based on the expression of T-cell biomarkers and expression of disease biomarkers determined in individual cells from a cell population isolated from the patient.

EXAMPLES

Example 1: Proof of Principle of Barcode Assembly on Cellular mRNA

In this example, the assembly of a compound barcodes was performed on isolated nucleic acids. The target sequences were rearranged immune sequences: T-cell receptor genes Alpha and Beta (TCRA and TCRB) and rearranged immunoglobulin gene (IgG). RNA was isolated from peripheral blood mononuclear cells (PBMC). The primer comprised a polyT sequence and a universal PCR primer binding site. The first strand cDNA synthesis protocol (Single Cell and cDNA Synthesis) and the primer sequences were obtained from New England BioLabs (Ipswich, Mass.). Three samples were processed as follows:

Sample 1: Barcode subunit 1 (SEQ ID NO: 1)+Barcode subunit 2 (SED ID NO: 2); Sample 2: Barcode subunit 1 (SEQ ID NO: 1)+Barcode subunit 2 (SED ID NO: 2)+enzyme mix; Sample 3: Only Barcode subunit 1 (SEQ ID NO: 1). Sample 2 was processed through sequencing with gene-specific primers for TCR A/B or IgG.

The following barcode subunits were used:

```
Barcode subunit 1 (TSO_1_01)
                                            (SEQ ID NO: 1)
WNNANCACACTGCTGACNWNrGrGrG  (rG is riboguanosine)

Barcode subunit 2 (TSO_nano_i7_11)
                                            (SEQ ID NO: 2)
/5Me-isodC/GTGACTGGAGTTCAGACGTGTGCTCTTCCGATCTNNWCACACTGC TGACWGrGrGrG 5-methyl-iso-deoxycytosine
```

5-methyl-iso-deoxycytosine

The reactions were subjected to the following temperature profile:
4C 1 min
42C 75 min
4C~add second barcode subunit
42C 10 min
72C 10 min
4C~

After reverse transcription and barcode assembly, the reactions were subjected to PCR amplification with a gene-specific primer for TCRA, TCRB and IgG (SEQ ID Nos. 3, 4, 5) opposite a universal primer (SEQ ID NO: 6). Amplicons had the following structure:

[Universal primer-BC2-BC1-gene sequence-gene-specific primer]

The amplification primers comprised a gene-specific sequence, a barcode sequence (UMI) and Illumina-specific adaptor sequence.

```
TCRA primer (TCRA_i501)
                                            (SEQ ID NO: 3)
5'-AATGATACGGCGACCACCGAGATCTACAC

TATAGCCTACACTCTTTCCCTACACGACGCTCTTCCGATCT

NNNNNNGGCAGGGTCAGGGTTCTGGATA-3'

TCRB primer (TCRB_i501)
                                            (SEQ ID NO: 4)
5'-AATGATACGGCGACCACCGAGATCTACAC

TATAGCCTACACTCTTTCCCTACACGACGCTCTTCCGATCT

NNNNNNTGCTTCTGATGGCTCAAACACAGCG-3'

IgG primer (IgG_503)
                                            (SEQ ID NO: 5)
AATGATACGGCGACCACCGAGATCTACACCCTATCCTACACTCTTTCCCT

ACACGACGCTCTTCCGATCTNNNNNNNGTAGTCCTTGACCAGGCAGCC-3'

Universal primer (i_701)
                                            (SEQ ID NO: 6)
CAAGCAGAAGACGGCATACGAGATCGAGTAATGTGACTGGAGTTCAGAC

GTGTGCTCTTCCGATC*T (*T is an phosphorothioate nucleotide)
```

PCR amplification was performed using the Q5® Hot Start High-Fidelity 2X Master Mix (New England BioLabs (Ipswich, Mass.) using the temperature profile recommended by the manufacturer. Amplification products were purified using Kapa Pure Beads (Kapa Biosystems (Wilmington, Mass.) The purified amplification products were sequenced on Illumina MiSeq for sequencing. 2×300 bases read length. The reads were analyzed to detect barcode subunits 1 and 2 (BC1, BC2). Results are shown in the table below.

| Sample | Reads | Reads after trim | Reads w/BC2 | Reads w/BC1 | Reads w/BC1 and BC2 |
|---|---|---|---|---|---|
| TCR (A, B) | 20,957,207 | 17,655,439 | 12,303,223 | 4,094 | 2,760 |
| IgG | 1,936,143 | 1,487,284 | 1,055,728 | 352 | 85 |

---

We claim:

1. A method of detecting a plurality of target nucleic acids in a plurality of cells, the method comprising
   (a) contacting the plurality of cells in a sample with an oligonucleotide primer for each target nucleic acid in the presence of a nucleic acid polymerase having a terminal transferase activity and a template switch activity, and extending the oligonucleotide primer to form a copy strand having one or more non-templated nucleotides at the 3'-end of the copy strand capable of functioning as an anchoring site for a barcode subunit;
   (b) for each target nucleic acid in each cell of the plurality of cells, forming an extended copy strand comprising a cell-characteristic compound barcode on the copy strand by sequentially attaching a series of barcode subunits to the 3'-end of a copy strand, wherein each barcode subunit comprises a sequence complementary to the one or more non-templated nucleotides at the 3' end of the copy strand and a barcode, wherein each barcode subunit includes (i) one or more 5'-nucleotide isomers, and (ii) one or more $T_m$-modified nucleotides, and wherein the attaching of the barcode subunits is performed by a split-pool process comprising one or more rounds of:
      (i) distributing the sample into a first set of reaction volumes, each volume containing a first barcode subunit and a nucleic acid polymerase to extend the 3'-end of the copy strand to copy the first barcode subunit;
      (ii) combining the first set of reaction volumes into a pool; and
      (iii) distributing the pool into a second set of reaction volumes, each volume containing a second barcode subunit and a nucleic acid polymerase to further extend the 3'-end of the copy strand to copy the second barcode subunit; and
   (c) determining the sequence of the extended copy strands including the cell-characteristic compound barcodes, thereby detecting the plurality of target nucleic acids in the plurality of cells;
   wherein the method does not comprise a separation or encapsulation of the plurality of cells prior to or during the split-pool process.

2. The method of claim 1, further comprising a step of amplifying the extended copy strands including the cell-characteristic compound barcodes prior to sequencing.

3. The method of claim 2, wherein the oligonucleotide primer comprises universal amplification primer binding site.

4. The method of claim 2, wherein the last barcode subunit to be copied comprises a universal amplification primer binding site.

5. The method of claim 1, wherein the oligonucleotide primer comprises a unique molecular identifier.

6. The method of claim 1, wherein the target nucleic acid is RNA.

7. The method of claim 6, wherein the target nucleic acid is messenger RNA.

8. The method of claim 6, wherein the oligonucleotide primer comprises a poly-dT sequence.

9. The method of claim 1, wherein the oligonucleotide primer comprises a target-specific sequence.

10. The method of claim 1, wherein the nucleic acid polymerase is reverse transcriptase.

11. The method of claim 10, wherein the reverse transcriptase has reduced RNaseH activity.

12. The method of claim 1, wherein the one or more non-templated nucleotides is deoxycytosine.

13. The method of claim 1, wherein the one or more 5'-nucleotide isomers are each independently selected from the group consisting of isodC and isodG.

14. The method of claim 1, wherein the one or more Tm-modified nucleotides are each independently selected from the group consisting of 8-aza-7-Br-7-deaza-2,6-diaminopurine, 5-propynyl-dC, 8-aza-7-Br-7-deaza-dG, and 5-propynyl-dU.

15. The method of claim 1, wherein the method further comprises performing a target enrichment process.

16. A method of detecting a plurality of target nucleic acids in a plurality of cells, the method comprising
   (a) contacting the plurality of cells in a sample with an oligonucleotide primer for each target nucleic acid in the presence of a nucleic acid polymerase having a terminal transferase activity and a template switch activity, wherein the oligonucleotide primer includes a motif-specific sequence or a random sequence, and extending the oligonucleotide primer to form a copy strand having one or more non-templated nucleotides at the 3'-end of the copy strand capable of functioning as an anchoring site for a barcode subunit;
   (b) for each target nucleic acid in each cell of the plurality of cells, forming an extended copy strand comprising a cell-characteristic compound barcode on the copy strand by sequentially attaching a series of barcode subunits to the 3'-end of a copy strand, wherein each barcode subunit comprises a sequence complementary to the one or more non-templated nucleotides at the 3' end of the copy strand and a barcode, wherein each barcode subunit includes one or more 5'-nucleotide isomers, and the attaching step is performed by a split-pool process comprising one or more rounds of:
      (i) distributing the sample into a first set of reaction volumes, each volume containing a first barcode subunit and a nucleic acid polymerase to extend the 3'-end of the copy strand to copy the first barcode subunit;
      (ii) combining the first set of reaction volumes into a pool; and
      (iii) distributing the pool into a second set of reaction volumes, each volume containing a second barcode subunit and a nucleic acid polymerase to further extend the 3'-end of the copy strand to copy the second barcode subunit; and
   (c) determining the sequence of the extended copy strands including the cell-characteristic compound barcodes, thereby detecting the plurality of target nucleic acids in the plurality of cells;
   wherein the method does not comprise a separation or encapsulation of the plurality of cells prior to or during the split-pool process.

17. The method of claim 16, wherein the motif-specific sequence is selected from the group consisting of a kinase domain specific sequence, a RAS family-specific sequence, and a tri-nucleotide repeat sequence.

18. The method of claim 16, wherein the oligonucleotide primer further comprises a unique molecular identification sequence.

19. A method of detecting a plurality of target nucleic acids in a plurality of cells, the method comprising
   (a) contacting the plurality of cells in a sample with an oligonucleotide primer for each target nucleic acid in the presence of a nucleic acid polymerase having a terminal transferase activity and a template switch activity, wherein the oligonucleotide primer includes a universal capture sequence, and extending the oligonucleotide primer to form a copy strand having one or more non-templated nucleotides at the 3'-end of the copy strand capable of functioning as an anchoring site for a barcode subunit;

(b) for each target nucleic acid in each cell of the plurality of cells, forming an extended copy strand comprising a cell-characteristic compound barcode on the copy strand by sequentially attaching a series of barcode subunits to the 3'-end of a copy strand, wherein each barcode subunit comprises a sequence complementary to the one or more non-templated nucleotides at the 3' end of the copy strand and a barcode, wherein each barcode subunit includes one or more 5'-nucleotide isomers, and the attaching step is performed by a split-pool process comprising one or more rounds of:

(i) distributing the sample into a first set of reaction volumes, each volume containing a first barcode subunit and a nucleic acid polymerase to extend the 3'-end of the copy strand to copy the first barcode subunit;

(ii) combining the first set of reaction volumes into a pool; and (iii) distributing the pool into a second set of reaction volumes, each volume containing a second barcode subunit and a nucleic acid polymerase to further extend the 3'-end of the copy strand to copy the second barcode subunit; and (c) determining the sequence of the extended copy strands including the cell-characteristic compound barcodes, thereby detecting the plurality of target nucleic acids in the plurality of cells;

wherein the method does not comprise a separation or encapsulation of the plurality of cells prior to or during the split-pool process.

20. The method of claim 19, wherein the method further comprises performing a target enrichment process.

* * * * *

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: single strand
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 1
wnnwcacact gctgacnwng gg                                      22

<210> SEQ ID NO 2
<211> LENGTH: 55
<212> TYPE: DNA
<213> ORGANISM: Artificial Sequence
<220> FEATURE:
<223> OTHER INFORMATION: single strand
<220> FEATURE:
<221> NAME/KEY: misc_feature
<222> LOCATION: (36)..(37)
<223> OTHER INFORMATION: n is a, c, g, or t
```

<400> SEQUENCE: 2
cgtgactgga gttcagacgt gtgctcttcc gatctnnwca cactgctgac wgggg     55

<210> SEQ ID NO 3
<211> LENGTH: 98
<212> TYPE: DNA
<213> ORGANISM: Artificial Sequence
<220> FEATURE:
<223> OTHER INFORMATION: single strand
<220> FEATURE:
<221> NAME/KEY: misc_feature
<222> LOCATION: (71)..(76)
<223> OTHER INFORMATION: n is a, c, g, or t

<400> SEQUENCE: 3
aatgatacgg cgaccaccga gatctacact atagcctaca ctctttccct acacgacgct     60
cttccgatct nnnnnnggca gggtcagggt tctggata     98

<210> SEQ ID NO 4
<211> LENGTH: 101
<212> TYPE: DNA
<213> ORGANISM: Artificial Sequence
<220> FEATURE:
<223> OTHER INFORMATION: single strand
<220> FEATURE:
<221> NAME/KEY: misc_feature
<222> LOCATION: (71)..(76)
<223> OTHER INFORMATION: n is a, c, g, or t

<400> SEQUENCE: 4
aatgatacgg cgaccaccga gatctacact atagcctaca ctctttccct acacgacgct     60
cttccgatct nnnnnntgct tctgatggct caaacacagc g     101

<210> SEQ ID NO 5
<211> LENGTH: 97
<212> TYPE: DNA
<213> ORGANISM: Artificial Sequence
<220> FEATURE:
<223> OTHER INFORMATION: single strand
<220> FEATURE:
<221> NAME/KEY: misc_feature
<222> LOCATION: (71)..(76)
<223> OTHER INFORMATION: n is a, c, g, or t

<400> SEQUENCE: 5
aatgatacgg cgaccaccga gatctacacc ctatcctaca ctctttccct acacgacgct     60
cttccgatct nnnnnngtag tccttgacca ggcagcc     97

<210> SEQ ID NO 6
<211> LENGTH: 66
<212> TYPE: DNA
<213> ORGANISM: Artificial Sequence
<220> FEATURE:
<223> OTHER INFORMATION: single strand

<400> SEQUENCE: 6
caagcagaag acggcatacg agatcgagta atgtgactgg agttcagacg tgtgctcttc     60
cgatct     66